United States Patent [19]

Behr

[11] 4,423,197

[45] Dec. 27, 1983

[54] CYCLIC PERFLUOROALIPHATIC-DISULFONIC ACID ANHYDRIDES AND SULFONAMIDE DERIVATIVES THEREOF

[75] Inventor: Fred E. Behr, St. Paul, Minn.

[73] Assignee: Minnesota Mining and Manufacturing Company, St. Paul, Minn.

[21] Appl. No.: 462,668

[22] Filed: Jan. 31, 1983

Related U.S. Application Data

[62] Division of Ser. No. 326,422, Dec. 1, 1981, Pat. No. 4,386,214, which is a division of Ser. No. 229,871, Jan. 30, 1981, Pat. No. 4,329,478.

[51] Int. Cl.$^3$ .................... C08F 4/00; C07C 143/74
[52] U.S. Cl. .................... 526/220; 564/85; 528/21; 528/23; 528/90; 528/408; 526/225
[58] Field of Search ............. 526/220, 225; 564/85; 528/21, 23, 90, 408

[56] References Cited

U.S. PATENT DOCUMENTS

| | | | |
|---|---|---|---|
| 2,732,398 | 6/1956 | Brice et al. | 260/503 |
| 3,346,606 | 10/1967 | Ward | 260/429 R |
| 3,347,676 | 10/1967 | Cripps | 430/280 |
| 3,586,616 | 6/1971 | Kropp | 526/225 |
| 3,803,112 | 4/1974 | Engelhardt et al. | 526/220 |
| 3,842,019 | 10/1974 | Kropp | 528/90 |
| 4,031,036 | 6/1977 | Koshor | 526/220 |
| 4,080,391 | 3/1978 | Tsumura et al. | 568/899 |
| 4,247,674 | 6/1981 | Koshor et al. | 528/21 |
| 4,387,222 | 6/1973 | Koshor | 528/408 |

FOREIGN PATENT DOCUMENTS

| | | |
|---|---|---|
| 45-28584 | 7/1970 | Japan ............. 526/225 |
| 1120304 | 7/1968 | United Kingdom . |
| 2051831 | 1/1981 | United Kingdom . |
| 2053902 | 2/1981 | United Kingdom . |

OTHER PUBLICATIONS

Modern Paints & Coatings, Oct. 1980, pp. 88–92.
Chemical Reviews 77, No. 1, 69–82 Howells et al.
Multi-Sulfur and Sulfur and Oxygen Five and Six Membered Heterocycles 1966 Interscience, John Wiley, Journal of Org. Chem. vol. 44, No. 2, 1979, pp. 343–345.

Primary Examiner—Joseph L. Schofer
Assistant Examiner—Peter F. Kulkosky
Attorney, Agent, or Firm—Donald M. Sell; James A. Smith; David R. Cleveland

[57] ABSTRACT

Cyclic perfluoroaliphaticdisulfonic acid anhydrides, sulfonamide derivatives thereof, a process for making the same, curable compositions containing cyclic perfluoroaliphaticdisulfonic acid anhydrides or sulfonamide derivatives thereof and cationically-sensitive monomers, and a process for using cyclic perfluoroaliphaticdisulfonic acid anhydrides or sulfonamide derivatives thereof as catalysts for the cure of cationically-sensitive monomers.

10 Claims, No Drawings

CYCLIC PERFLUOROALIPHATIC-DISULFONIC ACID ANHYDRIDES AND SULFONAMIDE DERIVATIVES THEREOF

This is a division of application Ser. No. 326,422 filed Dec. 1, 1981 now U.S. Pat. No. 4,386,214, which in turn is a division of Ser. No. 229,871 filed Jan. 30, 1981 now U.S. Pat. No. 4,329,478.

TECHNICAL FIELD

This invention relates to cyclic fluorocarbon anhydrides, sulfonamide derivatives thereof, and a process for their synthesis. In another aspect, this invention relates to curable compositions containing cationically-sensitive monomers, such as epoxides, and said cyclic fluorocarbon anhydrides or sulfonamide derivatives thereof. In yet another aspect, this invention relates to a process for curing cationically-sensitive monomers, utilizing as catalyst said cyclic fluorocarbon anhydrides or sulfonamide derivatives thereof.

BACKGROUND ART

Processes of polymerizing and curing cationically-sensitive monomers such as cyclic ethers (e.g., epoxides), vinyl ethers, and N-vinyl compounds, in the presence of catalysts, specifically Lewis acids, such as boron trifluoride, aluminum chloride, and the like, are well known. However, many of these catalysts are highly corrosive to various substrates such as metals. Other known catalysts for the polymerization of cationically sensitive monomers are undesirably toxic. Further, many of these acid catalysts rapidly catalyze the polymerization of the monomers with which they are admixed and cannot be used where a definite or prolonged shelf life and/or pot life is desired or required. Though some of these prior art acid catalysts can be used in a latent form, e.g. $BF_3 \cdot NH_2C_2H_5$, their latency is affected by moisture and prolonged latency is difficult to achieve; in addition, when these latent catalysts are activated, this gives rise to the aforementioned objectionable corrosiveness. Also, many known catalysts are not effective for polymerization of a broad range of cationically-sensitive monomers, e.g., for polymerization of both epoxides and cyclic siloxanes.

Various linear perfluoroaliphaticsulfonic acid anhydrides of the formula $(RSO_2)_2O$, where R is perfluoroalkyl, are described in U.S. Patent No. 2,732,398. U.K. Patent No. 1,120,304 discloses the use of the anhydride of trifluoromethanesulfonic acid as a catalyst for use in the polymerization of various cationically-sensitive monomers.

The utility of linear fluorocarbon sulfonic acid anhydrides (e.g., those derived from monofunctional perfluoroaliphaticsulfonic acids) as perfluoroaliphaticsulfonylation or acylation agents is also known. Use of the anhydride $(CF_3SO_2)_2O$ as a trifluoromethanesulfonylation agent for formation of trifluoromethanesulfonamides by reaction with ammonia or amines is disclosed in Chemical Reviews, 77, 69–92 (1977). T. R. Forbus and J. C. Martin, J. Org. Chem., 44, 313 (1979) have disclosed the preparation of the mixed anhydride, $CF_3SO_2OC(O)CF_3$, and its use as a trifluoroacetylation reagent for aromatic compounds. In these reactions, however, the above linear anhydrides produce not only the desired trifluoromethanesulfonylation or acylation product but also produce an equivalent amount of trifluoromethanesulfonic acid or salt thereof as by-product. For example, the reaction of $(CF_3SO_2)_2O$ with ammonia provides trifluoromethanesulfonamide and an equivalent amount of the ammonium salt of trifluoromethanesulfonic acid as by-product. Such by-product is undesirable because of unfavorable economics in the preparation of the desired product.

Cyclic fluorocarbon acid anhydrides are highly desirable compositions since, in contrast to the above linear anhydrides, reaction of cyclic anhydrides with reagents such as ammonia or amines can produce useful difunctional products by ring-opening reactions without formation of the above-described undesirable by-products. Very few such cyclic anhydrides are known, however, because of many factors such as ring instability, or decomposition, e.g., decarboxylation, during the process of ring formation, or because of the inability of many difunctional acids to undergo ring closure by dehydration. Cyclic anhydrides such as perfluorosuccinic acid anhydride are well known and provide useful products by ring-opening reactions such as reaction with ammonia to produce ammonium salts of the perfluorocarboxylic acids containing terminal carboxamido ($CONH_2$) functional groups. However, such cyclic anhydrides or their amide derivatives do not exhibit the catalytic properties of the cyclic anhydrides or sulfonamide derivatives of the invention described below.

The use of ammonia or amine salts of monofunctional perfluoroaliphaticsulfonic acids as latent catalysts for the polymerization of cationically-sensitive monomers is well known, see U.S. Pat. No. 3,842,019 and R. R. Alm, Modern Paint and Coatings, October, 1980, pages 88–92. However, the salts described in these references do not include a second functional group in the molecule (e.g., a sulfonamido group) as found in the ammonium or organoammonium salts of this invention.

DISCLOSURE OF INVENTION

The present invention provides, in one aspect, cyclic anhydrides of perfluoroaliphaticdisulfonic acids, having the formula:

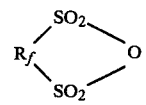

wherein $R_f$ is perfluoroalkylene having 2 to 5 backbone or catenary carbon atoms or perfluorocycloalkylene having 4 to 7, preferably 6, ring atoms, $R_f$ optionally being substituted by one or more, e.g., one to three, straight chain, branched, or cyclic perfluoroalkyl groups of 1 to 12, and preferably 1 to 4 carbon atoms, with $R_f$ having a total of up to 14 carbon atoms. Preferably $R_f$ has the formula $-CF_2-_m$ where m is 2 to 4.

The present invention also provides a process for the preparation by ring formation of said cyclic anhydrides of perfluoroaliphaticdisulfonic acids, comprising the steps of:

(a) mixing perfluoroaliphaticdisulfonic acid precursor with excess phosphorus pentoxide;

(b) heating the resulting mixture to dehydrate and cyclize said perfluoroaliphaticdisulfonic acid under anhydrous conditions; and (c) recovering said cyclic anhydride under anhydrous conditions from the resulting reacted mixture.

The invention further provides sulfonamide derivatives of said cyclic anhydrides, which sulfonamides are useful as latent catalysts for the polymerization of cationically-sensitive monomers. Said sulfonamides are prepared by reacting one or more of said cyclic anhydrides or perfluoroaliphaticdisulfonic acids with one or more protonic nitrogenous base having a $pK_b$ of less than about 13.2. The preferred sulfonamides have the formula:

$$R^1R^2NSO_2R_fSO_3^-H_2N^+R^1R^2 \quad \text{II}$$

wherein $R_f$ is as defined above, and each $R^1$ and $R^2$ is independently hydrogen, or a monovalent organic radical (preferably alkyl, alkoxy, alkenyl, cycloalkyl, aryl, or aryloxy, having 1 to 10 carbon atoms) which can be the same as or different from any other $R^1$ or $R^2$, or each $R^1$ and $R^2$ bonded to the same N atom can combine with one another to form a cyclic structure containing the N atom, and $R^1$ and $R^2$ can contain from 1 to about 20 carbon atoms, can be straight chain, branched or cyclic, can be saturated, unsaturated or aromatic, can contain skeletal or catenary hetero atoms, i.e., atoms other than carbon (e.g., oxygen or sulfur), and can be unsubstituted or substituted with non-interfering moieties, i.e., moieties which do not interfere with the functioning of said sulfonamides as latent acid catalysts.

This invention also provides curable compositions, comprising cationically-sensitive monomers and a catalytically effective amount of said cyclic perfluoroaliphaticdisulfonic acid anhydride or said sulfonamide derivative thereof.

This invention also provides a process for the polymerization of cationically-sensitive monomers, comprising the steps of:

(a) mixing with said monomers a catalytically effective amount of said cyclic perfluoroaliphaticdisulfonic acid anhydride or said sulfonamide derivative thereof, thereby forming a mixture, and (b) allowing said mixture to polymerize, or heating said mixture to effect polymerization thereof.

DETAILED DESCRIPTION

In the practice of the present invention, said cyclic anhydrides of perfluoroaliphaticdisulfonic acids (hereinafter, for brevity, also designated as cyclic anhydrides) are preferably prepared by the dehydration and cyclization of the precursor hydrated perfluoroaliphaticdisulfonic acids (III, below), caused by heating the precursor acid in the presence of an excess of a suitable dehydrating agent, e.g., phosphorus pentoxide, as shown in Equation 1 below, at a temperature sufficient to provide efficient and controllable reaction between the precursor acid and phosphorus pentoxide. Such temperature is preferably about 100° to 180° C.

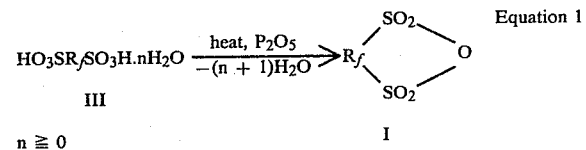

Equation 1

$n \geqq 0$

The resulting cyclic anhydride product is volatile and can be collected by distillation. The cyclic anhydride is prepared and stored under anhydrous conditions.

The amount of phosphorus pentoxide can vary depending on the amount of water of hydration present in the precursor perfluoroaliphaticdisulfonic acid hydrate. Generally, a one mole excess of phosphorus pentoxide is used with anhydrous precursor acid, but greater amounts such as up to a ten mole excess or more can be used with hydrates of the precursor acid.

An inert diluent such as sand, glass beads, or a high boiling fluorinated organic liquid is usually employed in the dehydration and cyclization reaction. The use of inert, fluorinated organic liquid diluent, having a boiling point which is substantially higher (e.g., 50° C.) than the boiling point of the desired cyclic anhydride product is preferred since such a diluent facilitates intimate contact of the reactants, efficient stirring, and good heat transfer, thus aiding in the rapid completion of the dehydration and cyclization reaction.

When fluorinated diluent is used, the volatile cyclic anhydride products can be isolated most conveniently on a small scale by purging the heated reaction flask with nitrogen gas and condensing the anhydride in a receiver cooled with "Dry Ice" to −78° C. Alternatively, the reaction mixture can be subjected to distillation.

The crude cyclic anhydride, obtained by any of the above procedures, can be additionally purified by redistillation, or can be used directly as an intermediate in the preparation of said sulfonamide derivatives. The cyclic anhydride should be stored in a sealed dry vessel to avoid hydrolysis through contact with water or water vapor until it is needed for use as a catalyst or for the preparation of sulfonamide derivatives. The presence of water or water vapor can cause the cyclic anhydride to hydrolyze and form the precursor linear acid hydrate.

The perfluoroaliphaticdisulfonic acid precursors for the preparation of the cyclic anhydrides of this invention can be obtained by means of a series of reactions, starting with the conversion of aliphaticdisulfonyl fluorides, $R_h(SO_2F)_2$ (where $R_h$ is the hydrocarbon analog of said $R_f$ radical) to the corresponding perfluoroaliphaticdisulfonyl fluorides, $R_f(SO_2F)_2$, by electrochemical fluorination in anhydrous hydrogen fluoride in accordance with the procedure described in U.S. Pat. No. 2,732,398. Alkaline hydrolysis of said perfluoroaliphaticdisulfonyl fluoride is performed by gradual addition thereof to a stirred solution of aqueous metal base such as carbonate or hydroxide of a metal such as sodium or potassium. Stirring is continued until completion of the reaction, followed by collection of the resulting solid salt product, rinsing of the salt with a small amount of cold water, and drying. The recovered product, $R_f(SO_3M)_2$ (where M is for example, Na or K), is dissolved in water, and the resulting solution is placed on a column of cationic ion exchange resin in the acid form (e.g., "Amberlite IR-120", commercially available from Rohm & Haas, Inc.). The column is eluted with distilled or deionized water, and the eluate is concentrated under reduced pressure at about 50° C. to constant weight to yield the desired acid hydrate precursor for the preparation of said cyclic anhydrides of Formula I, above.

Representative cyclic perfluoroaliphaticdisulfonic acid anhydrides of this invention include the following compounds:

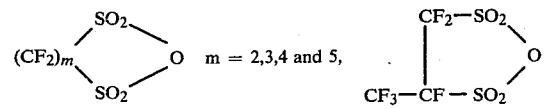

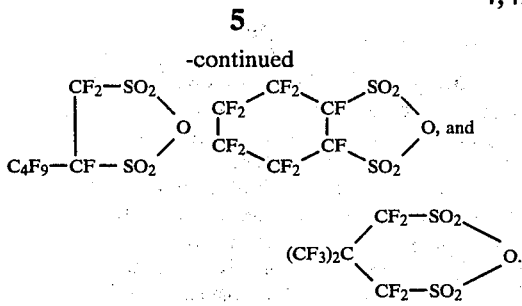

The sulfonamide derivatives of the cyclic anhydrides of the invention are obtained by reaction of the cyclic anhydride with a stoichiometric or excess amount of protonic nitrogenous base having a $pk_b$ less than about 13.2, such as ammonia, hydrazines, and organic amines containing at least one reactive hydrogen atom attached to nitrogen. The term "hydrazine" as used herein broadly includes hydrazine and hydrazine derivatives in which one or more hydrogen atoms bonded to nitrogen is replaced with $R^1$ or $R^2$ organic groups. Preferred nitrogenous bases have the formula $HNR^1R^2$, where $R^1$ and $R^2$ are as defined above. The cyclic anhydrides of this invention are reactive even with weakly basic amines such as diphenylamine (which has a $pk_b$ of 13.12).

The reaction of the cyclic anhydride with the protonic nitrogenous base can be carried out at a temperature which provides efficient and controlled reaction between the cyclic anhydride and nitrogenous base. Such temperature is generally about $-30°$ to $150°$ C., depending on the reactivity of the nitrogenous base. The reaction usually occurs readily at room temperature, with cooling sometimes being desirable to control the exotherm. The reactants can be combined in any order but a preferred method of conducting the amide formation reaction is by the slow addition of ammonia or amine to a stirred, cold (e.g., $0°$ C. to $10°$ C.) solution of the cyclic anhydride in an anhydrous inert solvent such as methylene chloride. Other suitable inert solvents include diethyl ether, isopropyl ether, and acetonitrile. The sulfonamide derivative is a salt in the form of an oil, grease, or solid. The oily or greasy salts are purified by decanting or evaporation of solvent. The solid salts can be isolated by filtration and purified by crystallization from an appropriate solvent or solvent mixture. Preferred sulfonamide derivatives are obtained by the reaction of the cyclic anhydride with ammonia or a primary or secondary organic amine.

Representative organic radicals $R^1$ or $R^2$ include methyl, ethyl, butyl, dodecyl, octadecyl, phenyl, o-tolyl, cyclopentyl, cyclohexyl, isopropyl, 2-ethylhexyl, propenyl, 2-butenyl, methoxymethyl, methoxyethyl, ethoxyethyl, ethoxybutyl, 4-methoxyphenyl, and eththioethyl. $R^1$ and $R^2$ together with N can be, for example, N-piperidyl or N-pyrrolidyl.

Representative organic amines having a $pk_b$ of about 13.2 or less and the formula $HNR^1R^2$ are described in "Handbook of Chemistry and Physics", 47th Edition, D-85 (1966-1967). Examples include methylamine, n-butylamine, n-octylamine, isobutylamine, cyclohexylamine, diethylamine, dioctylamine, diisobutylamine, diallylamine, glycine and its ethyl ester, aniline, N-methylaniline, p-chloroaniline, p-cyanoaniline, o-toluidine, m-aminophenol, diphenylamine, alpha-naphthylamine, morpholine, oxazolidine, thiazolidine, p-methoxyaniline, and the like. Such amines can contain substituent groups which are essentially non-reactive or less reactive than the amino group of the organic amine, including halogen, hydroxy, alkoxy, nitrile, carboxy and carboalkoxy.

Other protonic nitrogenous bases containing more than one basic —NH— or —NH$_2$— group can afford sulfonamide derivatives of this invention which are useful as catalysts. Such derivatives are generally more complex than the products represented by Formula II above and can be oligomers or polymers. Such nitrogenous bases include hydrazine, sym-dimethylhydrazine, methylhydrazine, methylhydrazinecarboxylate, guanidine, aminoguanidine, diethylenetriamine, triethylenetetramine, hexamethylenediamine, piperazine, polyethyleneimine, and the like.

Representative simple (i.e., non-oligomeric) sulfonamide derivatives of the cyclic anhydrides of this invention include the following:

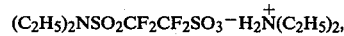

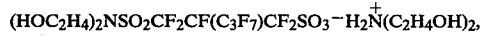

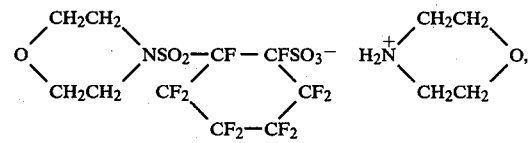

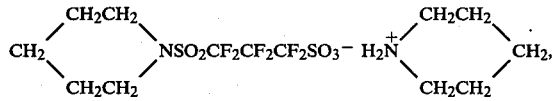

The cyclic anhydrides of this invention and sulfonamide derivatives thereof (sometimes collectively referred to hereafter as the compounds of the invention) are useful for the polymerization or curing of cationically-sensitive monomers. The term "monomers" as used herein includes not only low molecular weight cationically-sensitive materials, but also high molecular weight polymeric compositions, e.g., resins containing one or more cationically-sensitive polymerizable groups of the types described below, which in the presence of the compounds of this invention will undergo polymerization or crosslinking.

Said sulfonamide derivatives of the cyclic anhydrides of this invention are latent catalysts, particularly with respect to epoxides. The term "latent catalyst" as used herein means a catalyst which does not exhibit or manifest any substantial curing or catalytic effect on monomer admixed therewith during normal storage or handling of such mixtures until the mixture is subjected to heat for the purpose of activation, though some small or otherwise tolerable or insignificant curing of the monomer may take place before activation, as evidenced by a slight increase in viscosity. Similarly, a composition which has latency or is characterized as being latently curable is one which during the period prior to being heated to effect cure, exhibits little if any gelling, polymerization, etc., though some small or otherwise tolerable or insignificant curing may take place during such period.

The monomers that can be cured or polymerized with the compounds of this invention, using the latter in a catalytically effective amount, are those known to undergo cationic polymerization and include 1,2-, 1,3-, and 1,4-cyclic ethers (also designated as 1,2-, 1,3-, and 1-4-epoxides), vinyl ethers, N-vinyl compounds, ethylenically unsaturated hydrocarbons, cyclic formals, and cyclic organosiloxanes. An extensive list of cationically polymerizable monomers which can be used in this invention are given in U.S. Pat. Nos. 3,347,676 and 3,842,019.

The cyclic ethers which can be polymerized in accordance with this invention include those described in "Ring-Opening Polymerizations," Vol. 2, by Frisch and Reegan, Marcel Dekker, Inc. (1969). Suitable 1,2-cyclic ethers are the monomeric and polymeric types of epoxides. They can be aliphatic, cycloaliphatic, aromatic, or heterocyclic and will typically have an epoxy equivalency of from 1 to 6, preferably 1 to 3. Particularly useful are the aliphatic, cycloaliphatic, and glycidyl ether type 1,2-epoxides such as propylene oxide, epichlorohydrin, styrene oxide, vinylcyclohexene oxide, vinylcyclohexene dioxide, glycidol, butadiene oxide, glycidyl methacrylate, diglycidyl ether of bisphenol A, 3,4-epoxycyclohexylmethyl 3,4-epoxycyclohexanecarboxylate, 3,4-epoxy-6-methylcyclohexylmethyl 3,4-epoxy-6-methylcyclohexanecarboxylate, bis(3,4-epoxy-6-methylcyclohexylmethyl) adipate, dipentene oxide, epoxidized polybutadiene, 1,4-butanediol diglycidyl ether, polyglycidyl ether of phenolformaldehyde resole or novolak resin, resorcinol diglycidyl ether, and epoxy silicones, e.g., dimethylsiloxanes having cycloaliphatic epoxide or glycidyl ether groups. A wide variety of commercial epoxy resins is available and listed in "Handbook of Epoxy Resins" by Lee and Neville, McGraw-Hill Book Company, New York (1967) and in "Epoxy Resin Technology" by P. F. Bruins, John Wiley & Sons, New York (1968). Representative of the 1,3- and 1,4-cyclic ethers which can be polymerized in accordance with this invention are oxetane, 3,3-bis(-chloromethyl)oxethane, and tetrahydrofuran.

Another useful class of cationically-sensitive monomers which can be polymerized in accordance with this invention is represented by the general formula $CH_2=C(Y)XR'$, where X is —O— or —NR"— (where R" is hydrogen or lower alkyl), R' is hydrocarbyl, hydrocarbylcarbonyl, halohydrocarbyl, or hydroxyhydrocarbyl when X is oxygen, or R' is hydrocarbyl, hydrocarbylcarbonyl, or hydrocarbylsulfonyl when X is nitrogen, and Y is hydrogen, alkyl, aryl, or other hydrocarbyl, or R' (as hydrocarbylcarbonyl) and R" can be connected to form a 5- or 6-membered cyclic structure containing nitrogen as a hetero ring atom. The term "hydrocarbyl" is used herein in its usual sense to mean alkyl, alkenyl, aryl, cycloalkyl, cycloalkenyl, alkaryl, arylalkyl, and the like. In general, monomers of this type contain a vinyl group and are typified by vinyl alkyl ethers, such as vinyl methyl ether, vinyl ethyl ether, vinyl n-butyl ether, vinyl 2-chloroethyl ether, vinyl isobutyl ether, vinyl phenyl ether and vinyl 2-ethylhexyl ether, vinyl ethers of substituted aliphatic alcohols such as divinyl ether of butanediol, hydroxybutyl vinyl ether, and N-vinyl compounds such as N-vinyl-N-methyl octanesulfonamide and N-vinylpyrrolidone. A description of vinyl monomers and their use in preparing polymers is set forth in "Vinyl and Related Polymers," by Schildknecht, published by John Wiley & Sons, Inc., New York (1952).

Other cationically-sensitive monomers which can be polymerized in this invention include ethylenically unsaturated hydrocarbons such as isobutylene, 1,3-butadiene, isoprene, styrene, and divinylbenzene, especially the vinyl benzenes, cyclic formals such as trioxane, 1,3-dioxolane, 2-vinyl-1,3-dioxolane and methyl-1,3-dioxolane, and cyclic siloxanes which can contain various groups attached to the silicon atom such as a hydrocarbon radical (alkyl, aryl, alkaryl), an alkenyl hydrocarbon radical (vinyl, allyl or acryloyloxyalkyl), a halogenated hydrocarbon radical, a carboxy-containing hydrocarbon radical or ester group, a cyanohydrocarbon radical, hydrogen, halogen or a hydroxy group. Representative cyclic siloxanes are hexamethylcyclotrisiloxane, octamethylcyclotetrasiloxane, phenylheptamethylcyclotetrasiloxane, vinylheptamethylcyclotetrasiloxane, methacryloyloxymethylheptamethylcyclotetrasiloxane, bromomethylheptamethylcyclotetrasiloxane, 3-chloropropylheptamethylcyclotetrasiloxane, 1,2,3-tris(3,3,3-trifluoropropyl)-1,2,3-trimethylcyclotrisiloxane, acetoxymethylheptamethylcyclotetrasiloxane, cyanomethylheptamethylcyclotetrasiloxane, 1,2,3-trihydro-,1,2,3-trimethylcyclotrisiloxane, and chloroheptamethylcyclotetrasiloxane. Other known cyclic siloxanes are listed in "Chemistry and Technology of Silicones" by Walter Noll, Academic Press, New York (1968), Tables 41, 44 and 45.

The cyclic siloxanes can also be polymerized in the presence of relatively low molecular weight linear siloxanes such as hexamethyldisiloxane, chloropentamethyldisiloxane and octamethyltrisiloxane which serve to terminate the growing chain and provide stable fluids or fluids having reactive end groups.

There is a host of commercially available cationically-sensitive monomers which can be used in this invention. In particular, cyclic ethers which are readily available include propylene oxide, oxetane, epichlorohydrin, tetrahydrofuran, styrene oxide, vinylcyclohexene oxide, glycidol, glycidyl methacrylate, octylene oxide, phenyl glycidyl ether, 1,2-butane oxide, diglycidyl ether of bisphenol A (e.g., "Epon 828" and "DER 331"), vinylcyclohexene dioxide (e.g., "ERL-4206"), 3,4-epoxycyclohexylmethyl-3,4-epoxycyclohexanecarboxylate (e.g., "ERL-4221"), 3,4-epoxy-6-methylcyclohexylmethyl-3,4-epoxy-6-methylcyclohexanecarboxylate (e.g., "ERL-4201"), bis(3,4-epoxy-6-methylcyclohexylmethyl)-adipate (e.g., "ERL-4289"), aliphatic epoxy modified with polypropylene glycol (e.g., "ERL-4050" and "ERL-4052"), dipentene dioxide (e.g., "ERL-4269"), epoxidized polybutadiene (e.g., "Oxiron 2001"), silicone epoxy (e.g., "Syl-Kem 90"), 1,4-butanediol diglycidyl ether (e.g., "Araldite RD-2"), polyglycidyl ether of phenolformaldehyde novolak (e.g., "DEN-431," "Epi-Rez 521" and "DEN-438"), resorcinol diglycidyl ether (e.g., "Kopoxite"), polyglycol diepoxide (e.g., "DER 736"), polyacrylate epoxide (e.g., "Epocryl U-14"), urethane modified epoxide (e.g., "QX3599"), polyfunctional flexible epoxides (e.g., "Flexibilizer 151"), and mixtures thereof as well as mixtures thereof with co-curatives, curing agents, or hardeners which also are well known (see Lee and Neville and Bruins, supra). Representative of the co-curatives or hardeners which can be used are acid anhydrides such as nadic methyl anhydride, cyclopentanetetracarboxylic dianhydride, pyromellitic anhydride, cis-1,2-cyclohexanedicarboxylic anhydride, and mixtures thereof.

In general, the polymerization of cationically-sensitive monomers with the cyclic anhydrides of this invention can be carried out at room temperature for the majority of cationically-sensitive monomers, although low temperature (e.g., $-10°$ C.) or elevated temperatures (e.g., 30° to 200° C., preferably 50° to 100° C.), can be used to either subdue the exotherm of polymerization or to accelerate the polymerization. In the case of latent salt catalysts of this invention, temperatures generally in the range of 50° to 250° C., preferably from 80° to 150° C., can be used. The temperature of polymerization and amount of catalyst will vary and be dependent on the particular cationically-sensitive monomer used and the desired application of the polymerized or cured product.

The amount of cyclic anhydride or sulfonamide derivative thereof to be used as a catalyst in this invention (i.e., a catalytically effective amount) should be sufficient to effect polymerization of the cationically-sensitive monomer under the desired use conditions. Such amount generally will be in the range of about 0.01 to 20 weight percent, preferably 0.5 to 5 weight percent, and most preferably 1 to 2 weight percent, based on the weight of cationically-sensitive monomer.

Solvents can be used to assist in dissolution of the cyclic anhydride or sulfonamide derivative thereof in the cationically-sensitive monomer, and are preferred for use with sulfonamide derivatives. Representative solvents include acetone, methylene chloride, ethyl acetate, methyl ethyl ketone, acetonitrile, p-dioxane, and the dimethyl ether of ethylene glycol (glyme). In general, in compositions containing cyclic anhydride catalyst, basic solvents or basic impurities in the monomer are avoided to prevent deactivation of the anhydride catalyst.

The curable or polymerizable compositions of this invention, consisting of or consisting essentially of the cationically-sensitive monomer(s) and said cyclic anhydride or sulfonamide derivative thereof as catalyst, can be used for applications like those cationically-sensitive monomer systems cured with other catalysts, such as epoxides cured with $BF_3$ or the complex of $BF_3$ with diethyl ether. Also, curable compositions of the invention comprising cationically-sensitive monomer(s), said cyclic anhydride or sulfonamide derivative thereof as catalyst, and other adjuvants (e.g., fillers, reinforcements, pigments, extenders, plasticizers and surface modifying agents) can be prepared in the same manner as compositions containing cationically-sensitive monomers, other catalysts, and adjuvants. For example, the curable compositions of this invention can be used as adhesives, caulking and sealing compounds, casting and molding compounds, potting and encapsulating compounds, impregnating and coating compounds, etc., depending on the particular monomers and/or catalyst used. Where the catalyst is used in its latent form, the curable composition can be used as a one-component or cured-in-place system, such capability enhancing its use for the applications mentioned above. One particular application where such capability can be employed is in the electrical arts, where such latently curable compositions can be used to coat or impregnate for insulation or protective purposes electrical motor windings or coils, transformers, capacitors, electrical terminals, cables, and other electrical devices.

The curable epoxy composition of this invention can be used to make shaped articles of self-supporting, structural, filled or reinforced epoxy resin composites, such as glass fiber cloth reinforced epoxy resin composites, useful, for example, as repair materials. The various fillers, reinforcements, and other particulate materials to be mixed or coated with or dispersed in the curable compositions of this invention to make the composites of this invention, as well as methods of processing these materials in making the composites, and their applications, are those known to the art. In this connection, reference is made to "Modern Composite Materials," edited by Brautman and Krock, published by Addison-Wesley Publishing Company, Reading, Mass. (1967); and "Handbook of Fiberglass and Advanced Plastics Composites," edited by G. Lubin, published by Van Nostrand Reinhold Company, New York, N.Y. (1969).

The objects and advantages of this invention are further illustrated by the following examples, but the particular materials and amounts thereof recited in these examples as well as other conditions and details should not be construed to unduly limit this invention.

EXAMPLE 1

This example shows a general procedure useful for the preparation of cyclic anhydrides of this invention.

To a 500 ml, three-necked flask fitted with a mechanical stirrer, thermometer, condenser and addition funnel, and containing 54.7 g (0.97 mole) of KOH dissolved in 100 ml water, was added gradually over about 1 hour, with heating (about 80° C.) and stirring, 63.2 g (0.20 mole) of hexafluoro-1,3-propanedisulfonyl fluoride, $FO_2SCF_2CF_2CF_2SO_2F$. Heating and stirring were continued for about three more hours and the reaction mixture was allowed to cool overnight. The reaction product was filtered, washed with 25 ml of cold water, and allowed to air dry, yielding 78 g of fine, white crystals. Infrared analysis of the crystals was consistent with the structure hexafluoro-1,3-propanedisulfonic acid dipotassium salt, $KO_3SCF_2CF_2CF_2SO_3K$.

A 9.7 g sample of the salt was dissolved in 50 ml of warm water and placed in a 50 cm×2.5 cm glass column containing a 20 cm bed of ion exchange resin ("Amberlite IR-120") in the acid ($H^+$) form which had been previously prepared by treating the resin with 6 N hydrochloric acid and rinsing with distilled water. The column was eluted with distilled water. The first 100 ml of eluate were concentrated under reduced pressure to yield 7.5 g of clear liquid product. The identity of the product was established by infrared spectroscopy, fluorine NMR (Fnmr) analysis, and water determination, as the hexahydrate of hexafluoro-1,3-propanedisulfonic acid, $HO_3SCF_2CF_2CF_2SO_3H.6H_2O$. The acid hydrate partially crystallized on standing.

A mixture of 11.3 g (0.027 mole) of the above disulfonic acid hydrate (from another run) and 30 g of phosphorus pentoxide was heated to 130° C. under reduced pressure in a flask adapted for short-path distillation. A total of 4.3 g colorless liquid product was collected in a trap cooled with "Dry Ice" to $-78°$ C. The liquid product was redistilled, yielding a colorless, non-fuming liquid with a boiling range of 109°–110° at atmospheric pressure, $n_d^{22}$ 1.3562. The product is insoluble in water at room temperature, but hydrolyzes within a few minutes to give a homogeneous solution. Analytical data are consistent with the structure hexafluoro-1,3-propanedisulfonic acid anhydride,

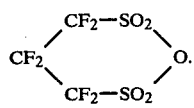

EXAMPLE 2

This example illustrates the preparation of a sulfonamide derivative of a cyclic anhydride of this invention.

About 1.0 g of the cyclic hexafluoro-1,3-propanedisulfonic acid anhydride of Example 1 was added dropwise to a stirred 1.0 g portion of piperidine which had been cooled to $-10°$ C. The dark crude solid product was recrystallized from an ethyl acetate/diethyl ether mixture to yield gold colored crystals, m.p. 86°-88° C.

The structure of the mixed sulfonamide-sulfonate salt,

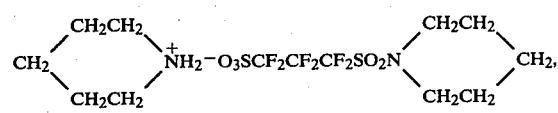

was established by infrared analysis.

EXAMPLE 3

A reaction product with ammonia was prepared by the slow addition of excess ammonia gas to an anhydrous methylene chloride solution of the cyclic anhydride prepared in Example 1. The resulting solid product was crystallized from a mixture of diethyl ether and carbon tetrachloride to yield white crystals, m.p. 168.5°-169° C. Elemental analysis, infrared analysis, and Fnmr spectra were consistent with the structure:

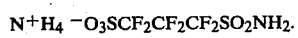

EXAMPLE 4

This example illustrates another method for carrying out the dehydration and cyclization reaction of Equation 1, above, utilizing an inert, high-boiling, fluorinated organic diluent.

To a stirred mixture of 30 g of phosphorus pentoxide in 75 ml of tris(perfluoroamyl)amine, $(C_5F_{11})_3N$, in a 250 ml, three-necked flask fitted with a thermometer, mechanical stirrer and nitrogen gas inlet, and connected to a trap cooled with "Dry Ice" to $-78°$ C., was added 5.0 g of hexafluoro-1,3-propanedisulfonic acid hexahydrate. The resulting mixture was heated over a one hour period to a maximum of 170° C. while stirring and purging with a slow stream of nitrogen. Warming the $-78°$ C. trap gave a colorless liquid weighing 2.4 g (69% yield). The infrared spectrum was consistent with the desired cyclic hexafluoro-1,3-propanedisulfonic acid anhydride.

EXAMPLE 5

Using the method of Example 1, cyclic tetrafluoro-1,2-ethanedisulfonic acid anhydride,

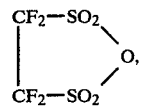

b.p. 100° to 101° C., was prepared. The identity of the liquid anhydride product was established by infrared and Fnmr analysis. The anhydride fumes in moist air, hydrolyzing to form the disulfonic acid hydrate precursor.

EXAMPLE 6

Using the method of Example 1, cyclic octafluoro-1,4-butanedisulfonic acid anhydride,

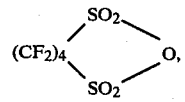

b.p. 126.5°-127.0° C., was prepared. The dehydration and cyclization reaction was carried out using sand in the reaction vessel.

EXAMPLE 7

Using the method of Example 1, cyclic decafluoro-1,5-pentanedisulfonic acid anhydride,

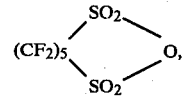

was prepared. The dehydration and cyclization reaction was carried out using sand in the reaction vessel.

EXAMPLE 8

A reaction product of the cyclic anhydride of Example 6 with ammonia was prepared by the gradual addition of ammonia gas to a methylene chloride solution of the cyclic anhydride. The product was a white powder. The mixed sulfonamide-ammonium salt structure, $NH_4^+ \ ^-O_3SCF_2-CF_2-CF_2-CF_2-SO_2NH_2$, was established by infrared analysis and Fnmr spectra.

The following examples (9-13) illustrate the utility of cyclic anhydrides of this invention as polymerization catalysts for cationically-sensitive monomers.

EXAMPLE 9

Polymerization of Tetrahydrofuran

In a 500 ml resin flask fitted with mechanical stirrer, thermometer and nitrogen gas inlet was placed 100 g of anhydrous tetrahydrofuran and 15 g of cyclohexane. The flask contents were cooled to 4° C. with an ice bath, then 2.0 g of hexafluoro-1,3-propanedisulfonic acid anhydride was added. A mildly exothermic polymerization reaction ensued, accompanied by increased viscosity of the reaction mixture. After one hour, the ice bath was removed. After three hours, stirring was very difficult. Additional cyclohexane (65 g) and 120 g of toluene were added to the reaction vessel and the resulting solution was mixed with 100 g of toluene which had been saturated with anhydrous ammonia. The resulting solution was stirred for one hour at room temperature with 16.7 g of anion exchange resin ("Amberlite IRA- 402", commercially available from Rohm and Haas, Inc.), then filtered to remove the resin particles. A sample of the —$NH_2$ terminated tetramethylene oxide polymer product, $H_2N(C_4H_8O)_nC_4H_8NH_2$, was isolated from solution and characterized by gel permeation chromatography.

EXAMPLE 10

Polymerization of an Aliphatic Diepoxide

To a small glass vial containing a solution of 2.0 g of 3,4-epoxycyclohexylmethyl-3,4-epoxycyclohexanecarboxylate ("ERL 4221" epoxide) in 2 ml of methylene chloride was added one drop of the cyclic anhydride of Example 9. A small quantity of solid formed initially, but there was no apparent viscosity increase after two days at room temperature. Heating at about 130° for 10 min. resulted in the formation of a dark, solid resinous product, useful as a potting resin.

EXAMPLE 11

Polymerization of Styrene

To a small glass vial containing a solution of 2.0 g of styrene in 2 ml of methylene chloride was added one drop of the cyclic anhydride of Example 9. After 0.75 hour, the solution was cloudy. After standing overnight, the solution was very viscous. A clear, tough polymer resulted after several days.

EXAMPLE 12

Polymerization of N-Vinyl Pyrrolidone

Using the method of Example 11, one drop of the cyclic anhydride of Example 9 was added to a solution of 2.0 g of N-vinyl pyrrolidone in 2 ml of methylene chloride. A viscous oil was obtained after four days.

EXAMPLE 13

Polymerization of Octamethylcyclotetrasiloxane

Using the method of Example 11, one drop of the cyclic anhydride of Example 9 was added to a solution of 2.0 g of octamethylcyclotetrasiloxane, [$(CH_3)_2SiO]_4$, in 2 ml of methylene chloride. The viscosity of the solution increased overnight. A solid polymer was obtained after four days.

Examples 14 and 15 show the utility of ammonium and organoammonium sulfonamidoperfluoroaliphaticsulfonates as latent catalysts for an epoxy resin.

EXAMPLE 14

In a glass vial was placed about 25 mg of $H_2NSO_2CF_2CF_2CF_2SO_3^-$ $N^+H_4$ (from Example 3) and 1.0 g "ERL 4221" epoxide. The salt dissolved in the epoxide at room temperature. There was no apparent change in viscosity of the epoxide/salt solution after 30 hours at room temperature, but on heating at 130° for 10 minutes, a clear, nearly colorless brittle solid formed.

EXAMPLE 15

In a glass vial was placed about 25 mg of $CH_3NHSO_2CF_2CF_2CF_2SO_3^-$ $H_2N^+CH_3$ (prepared using the method of Example 3, but with $CH_3NH_2$ in place of $NH_3$) and 1.0 g of "ERL 4221" epoxide. The salt dissolved at room temperature yielding a pale amber solution. There was no apparent reaction or viscosity change after 30 hours at room temperature, but on heating at 130° for 10 minutes, an amber, brittle solid was produced.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. Sulfonamides, useful as latent catalysts for the polymerization of cationically-sensitive monomers, comprising the reaction product of at least one cyclic anhydride of perfluoroaliphaticdisulfonic acids, having the formula:

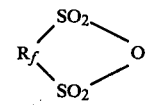

wherein $R_f$ is perfluoroalkylene having 2 to 5 catenary carbon atoms or perfluorocycloalkylene having 4 to 7 ring atoms, $R_f$ optionally being substituted by one or more straight chain, branched, or cyclic perfluoroalkyl groups of 1 to 12 carbon atoms, with $R_f$ having a total of up to 14 carbon atoms, together with at least one protonic nitrogenous base having a $pk_b$ of less than about 13.2.

2. Sulfonamides, useful as latent catalysts for the polymerization of cationically-sensitive monomers, comprising compounds having the formula:

wherein $R_f$ is perfluoroalkylene having 2 to 5 catenary carbon atoms or perfluorocycloalkylene having 4 to 7 ring atoms, $R_f$ optionally being substituted by one or more straight chain, branched, or cyclic perfluoroalkyl groups of 1 to 12 carbon atoms, with $R_f$ having a total of up to 14 carbon atoms, and each $R^1$ and $R^2$ is independently hydrogen, or a monovalent organic radical which can be the same as or different from any other $R^1$ or $R^2$, or each $R^1$ and $R^2$ bonded to the same N atom can combine with one another to form a cyclic structure containing the N atom, and $R^1$ and $R^2$ can contain from 1 to about 20 carbon atoms, can be straight chain, branched or cyclic, can be saturated, unsaturated or aromatic, can contain skeletal or catenary hetero atoms other than carbon and can be unsubstituted or substituted with non-interfering moieties.

3. Curable compositions, comprising cationically-sensitive monomers and a catalytically effective amount of cyclic anhydride of perfluoroaliphaticdisulfonic acids, having the formula:

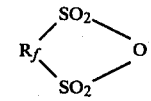

wherein $R_f$ is perfluoroalkylene having 2 to 5 catenary carbon atoms or perfluorocycloalkylene having 4 to 7 ring atoms, $R_f$ optionally being substituted by one or more straight chain, branched, or cyclic perfluoroalkyl groups of 1 to 12 carbon atoms, with $R_f$ having a total of up to 14 carbon atoms.

4. Curable compositions according to claim 3, wherein said cationically-sensitive monomer is selected from the group consisting of 1,2-, 1,3-, and 1,4-cyclic ethers, vinyl ethers, N-vinyl compounds, ethylenically unsaturated hydrocarbons, cyclic formals, and cyclic organosiloxanes.

5. Curable compositions according to claim 3, wherein said cationically-sensitive monomer comprises epoxide having an epoxy equivalency of 1 to 6.

6. Curable compositions, comprising cationically-sensitive monomers and a catalytically effective amount of sulfonamide according to claim 2.

7. Curable compositions according to claim 6, wherein said cationically-sensitive monomer is selected from the group consisting of 1,2-, 1,3-, and 1,4-cyclic ethers, vinyl ethers, N-vinyl compounds, ethylenically unsaturated hydrocarbons, cyclic formals, and cyclic organosiloxanes.

8. Curable compositions according to claim 6, wherein said cationically-sensitive monomer comprises epoxide having an epoxy equivalency of 1 to 6.

9. A process for polymerizing cationically-sensitive monomers using a cyclic anhydride of perfluoroaliphaticdisulfonic acids, having the formula:

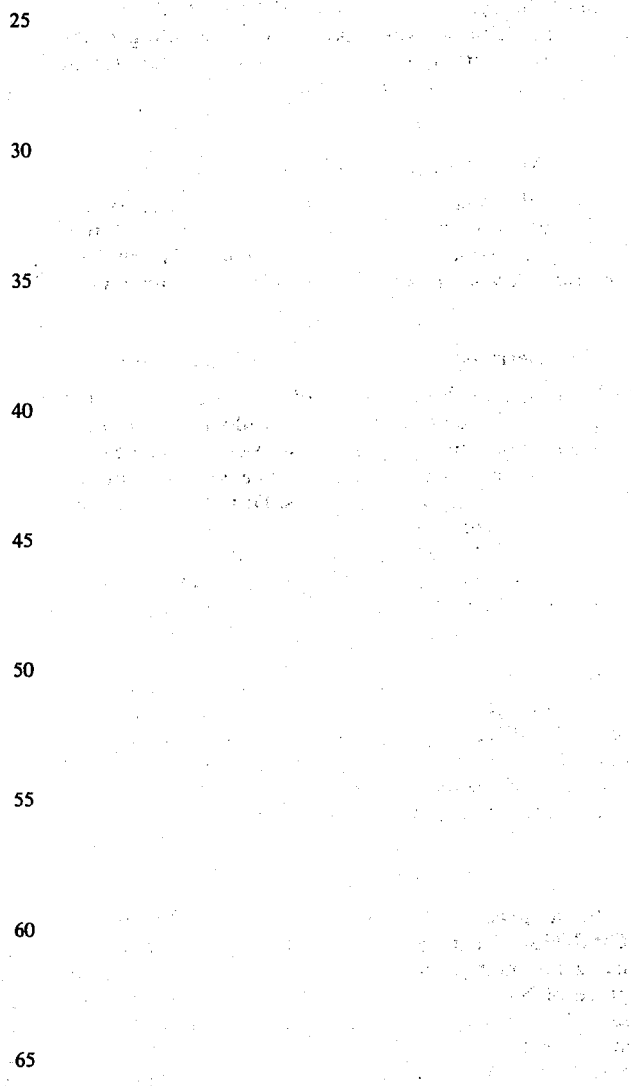

wherein $R_f$ is perfluoroalkylene having 2 to 5 catenary carbon atoms or perfluorocycloalkylene having 4 to 7 ring atoms, $R_f$ optionally being substituted by one or more straight chain, branched, or cyclic perfluoroalkyl groups of 1 to 12 carbon atoms, with $R_f$ having a total of up to 14 carbon atoms, comprising the steps of:
  (a) mixing with said monomers a catalytically effective amount of said cyclic anhydride or sulfonamide derivative thereof, thereby forming a mixture; and
  (b) allowing said mixture to polymerize or heating said mixture to effect polymerization thereof.

10. A process according to claim 9, wherein said cationically-sensitive monomer comprises epoxide having an epoxy equivalency of from 1 to 6.

* * * * *